United States Patent
Li

(10) Patent No.: US 9,980,876 B2
(45) Date of Patent: May 29, 2018

(54) METHODS AND DEVICES TO PROVIDE PERSISTENT HOT TACTILE EXPERIENCE

(71) Applicant: Qingyuan Li, Beijing (CN)

(72) Inventor: Qingyuan Li, Beijing (CN)

( * ) Notice: Subject to any disclaimer, the term of this patent is extended or adjusted under 35 U.S.C. 154(b) by 254 days.

(21) Appl. No.: 14/678,994

(22) Filed: Apr. 5, 2015

(65) Prior Publication Data
US 2016/0287467 A1    Oct. 6, 2016

(51) Int. Cl.
*A61F 5/00* (2006.01)
*A61H 19/00* (2006.01)
*A61F 7/00* (2006.01)
*A61H 37/00* (2006.01)

(52) U.S. Cl.
CPC ............... *A61H 19/00* (2013.01); *A61F 7/00* (2013.01); *A61H 37/00* (2013.01); *A61H 2201/0207* (2013.01); *A61H 2201/0228* (2013.01); *A61H 2201/5015* (2013.01); *A61H 2201/5082* (2013.01); *A61H 2201/5097* (2013.01)

(58) Field of Classification Search
CPC .......... A61H 9/00; A61H 19/00; A61H 37/00; A61F 7/00; A61F 7/007
USPC ....................................................... 600/38–41
See application file for complete search history.

(56) References Cited

U.S. PATENT DOCUMENTS

| | | | | |
|---|---|---|---|---|
| 4,310,748 A | * | 1/1982 | Paulin | A47J 27/002 219/433 |
| 5,672,274 A | * | 9/1997 | Wheeler | A47J 27/21183 210/474 |
| 6,417,498 B1 | * | 7/2002 | Shields | A47J 36/2427 219/386 |

* cited by examiner

*Primary Examiner* — John Lacyk

(57) ABSTRACT

The present disclosure provides an electric heating device which can provide persistent hot tactile experience in male masturbation and meanwhile keep the insertion passage tight as long as possible. The device includes a electric heating kettle having at least two masturbator chambers and one lubrication chamber, a coaster, a transfer pipette having long and thin tube, a electrical thermometer. The present disclosure also provides a method to use hot masturbators rotationally. The present disclosure further provides a lubrication bottle embed with a transfer pipette and electric heating function.

7 Claims, 5 Drawing Sheets

US 9,980,876 B2

METHODS AND DEVICES TO PROVIDE PERSISTENT HOT TACTILE EXPERIENCE

FIELD OF INVENTION

The present invention is to provide persistent hot tactile experience in masturbation for males.

BACKGROUND OF INVENTION

Unlike female vibrators, male masturbators are consumables. It won't take too long to tear them up. There is no safe, affordable male masturbator integrated with electric heating function.

For example, heating rod is the most popular heating device for male masturbator, but it slowly melts the gel's central passage structure after several months of using, which is the key to provide tight, sucking feeling experience.

A second category includes heating blanket and customized heating pad. But it's hard to grip after the masturbator is rolled up by heating blanket or filled in with heating pad. And it's hard to customize for all different sizes of the male masturbators.

A third category includes hot water soaking or running through the inner passage if the second opening exists in another end. But it gets cold quickly after several minutes.

SUMMARY OF INVENTION

The object of the present invention is to improve experiences within the prior art relating to the male masturbator heating devices or methods:

Keep the insertion passage tight as long as possible;
Provide persistent hot tactile experience as long as needed;
Keep the original size of masturbator while using;
In accordance with all embodiments of the invention there is provided a device comprising:
Separated chambers to hold rotational masturbators from topple down;
Separated chambers to hold lubrication for run-through masturbator which has two orifices;
Electric heating base;
Coaster to connect to house current;
Temperature controlling circuit and thermo sensor;
Transfer pipette to fill the lubrication into the inner passages of the masturbators;
Electrical thermometer to measure the temperatures inside the passages of the masturbators;
Timer to prompt user the masturbators are ready for use;
In accordance with all embodiments of the invention there is provided a method comprising:
Rotational use of hot masturbators to provide persistent hot tactile experience as long as needed;
Separated lubrication heating for run-through masturbator which has two orifices;
Customizing final inner heat degree of the masturbators;
Customizing the thermal capacities of water for heating to accommodate different masturbators;
Using customized transfer pipette to release the lubrication at bottom of the inner passage, and keep the passage tight as long as possible;
Using timer to semi-automatically prompt user the masturbators are ready for use;

It should be understood, however, that this summary may not contain all aspects and embodiments of the present invention, that this summary is not meant to be limiting or restrictive in any manner, and that the invention as disclosed herein will be understood by one of ordinary skill in the art to encompass obvious improvements and modifications thereto.

BRIEF DESCRIPTION OF DRAWINGS

In FIG. 2, the top lid is opened, and it is closed in FIG. 3.

In accordance with common practice, the various described features are not drawn to scale and are drawn to emphasize features relevant to the present disclosure. Like reference characters denote like elements throughout the figures and text.

DETAILED DESCRIPTION

Figure 1A:
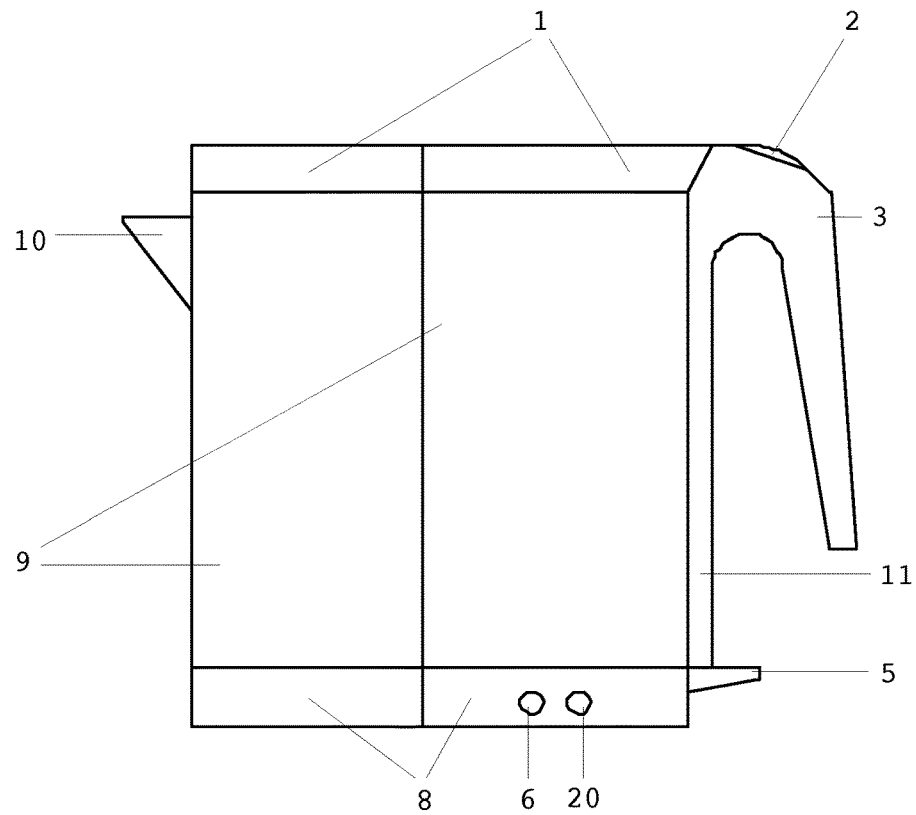
FIG. 1A is a side view of one exemplary embodiment of the present invention. Without the coaster.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the term "and/or" includes any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present invention.

It will be understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. It is to be understood that where the specification states that a component feature, structure, or characteristic "may", "might", "can" or "could" be included, that particular component, feature, structure, or characteristic is not required to be included.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The description will be made as to the embodiments of the present invention in conjunction with the accompanying drawings in FIGS. 1 to 8. Reference will be made to the drawing figures to describe the present invention in detail, wherein depicted elements are not necessarily shown to scale and wherein like or similar elements are designated by same or similar reference numeral through the several views and same or similar terminology.

All exemplary embodiments of the present invention comprises a electric heating kettle, a coaster, a transfer pipette and a electrical thermometer. If wireless electrical power of kilowatt level was available, the coaster would not be required anymore.

The kettle has at least two masturbator chambers 9. The masturbator chamber is cylinder in exemplary embodiments, but other shapes are possible. The masturbator chambers could be connected with each other through the bottom tangent planes, so the water could be poured easily through the outer masturbator chamber which has a nozzle 10.

The kettle also has a lubrication chamber 21 to heat the lubrication separately for masturbators which have two orifices like Fleshlight™ sleeves, otherwise lubrication would leak while be heated with the masturbators.

Figure 1B:
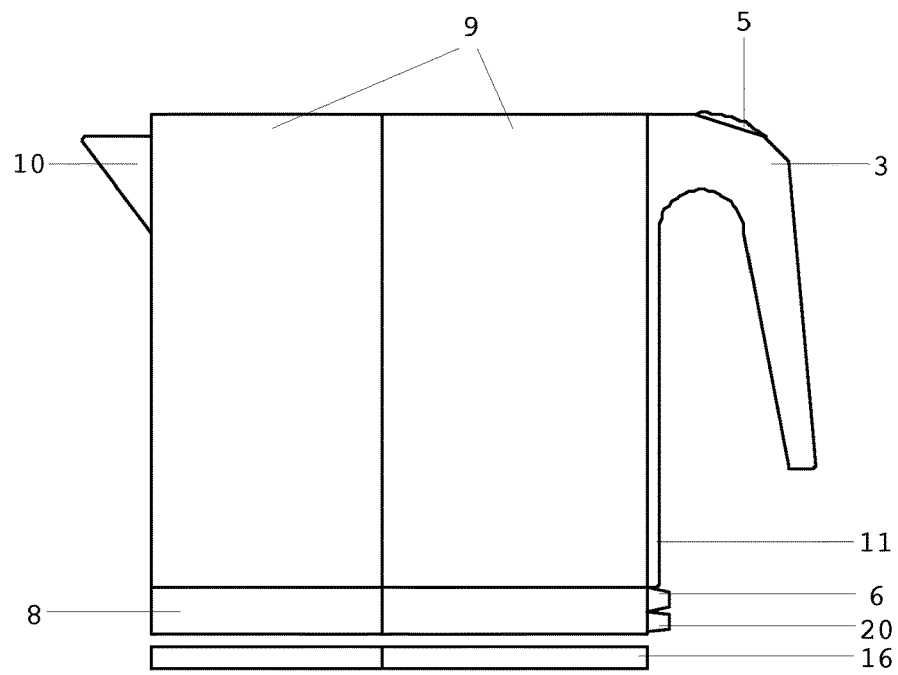
FIG. 1B is a exploded view of another exemplary embodiment of the present invention, which doesn't have a top lid. The bottom is a coaster.
Figure 2:
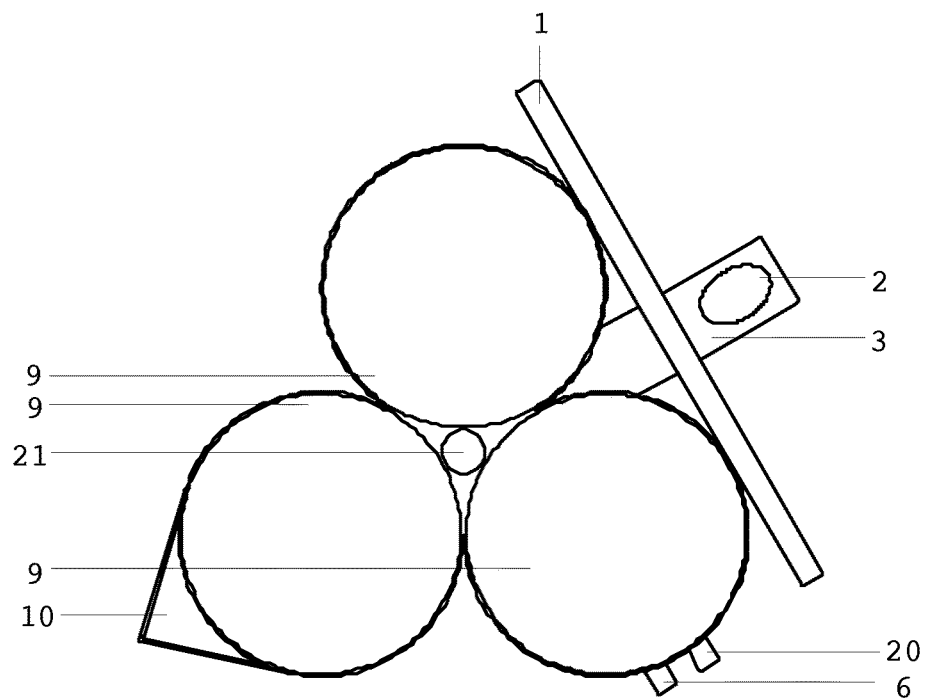
FIGS. 2 and 3 are top views of the first exemplary embodiment of the present invention.
Figure 3:
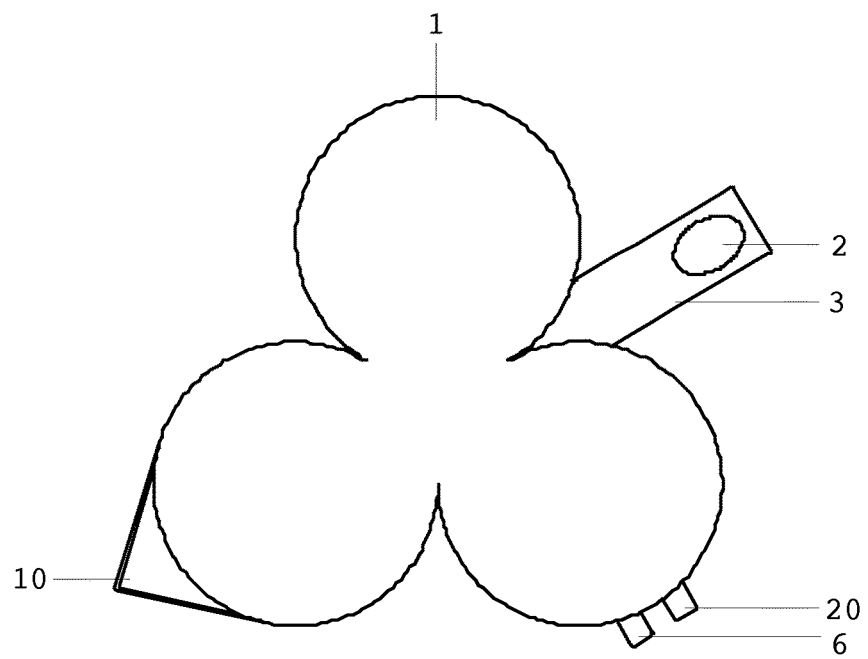
Figure 4:
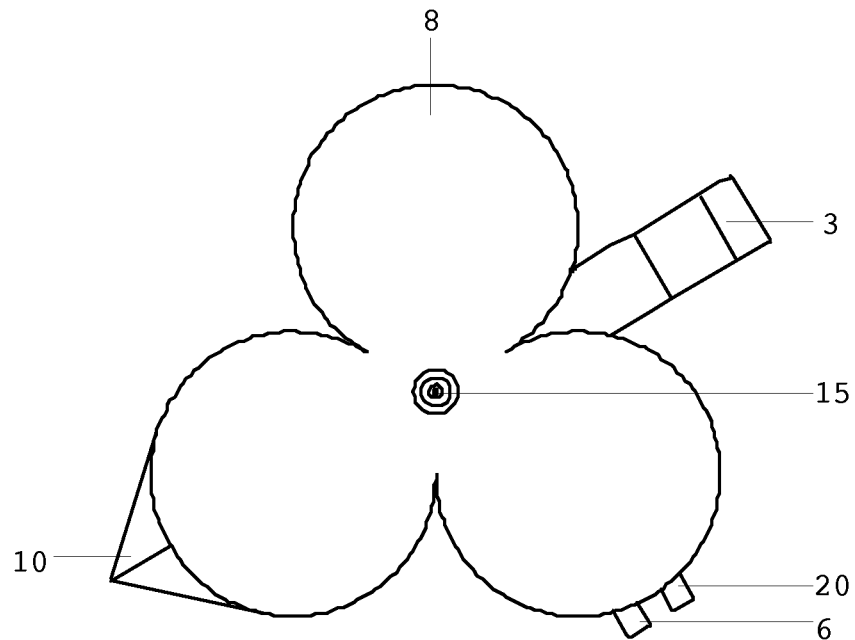
FIG. 4 is a bottom view of the first exemplary embodiment of the present invention.
Figure 5:
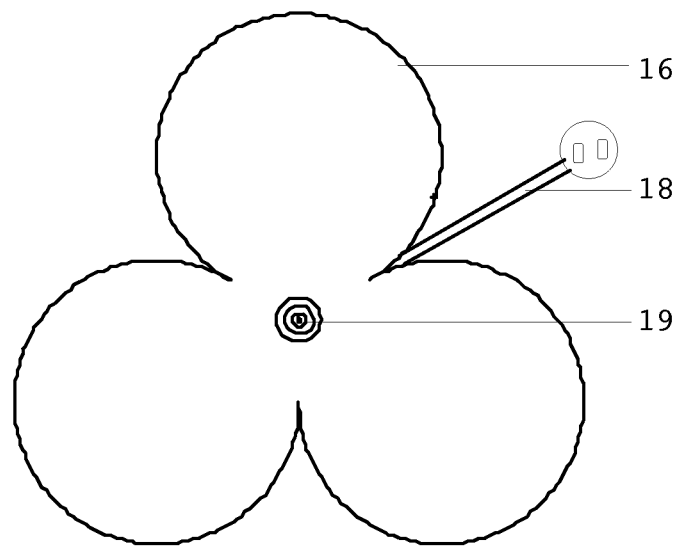
FIG. 5 is a top view of the coaster of an exemplary embodiment of the present invention.
Figure 6:
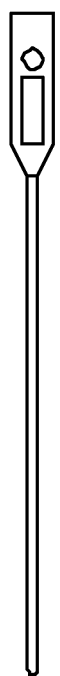
FIG. 6 is a front view of one electrical thermometer.
Figure 7:
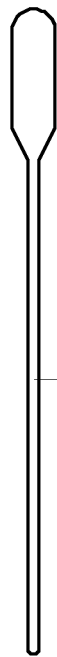
FIG. 7 is a front view of one transfer pipette.
Figure 8A:
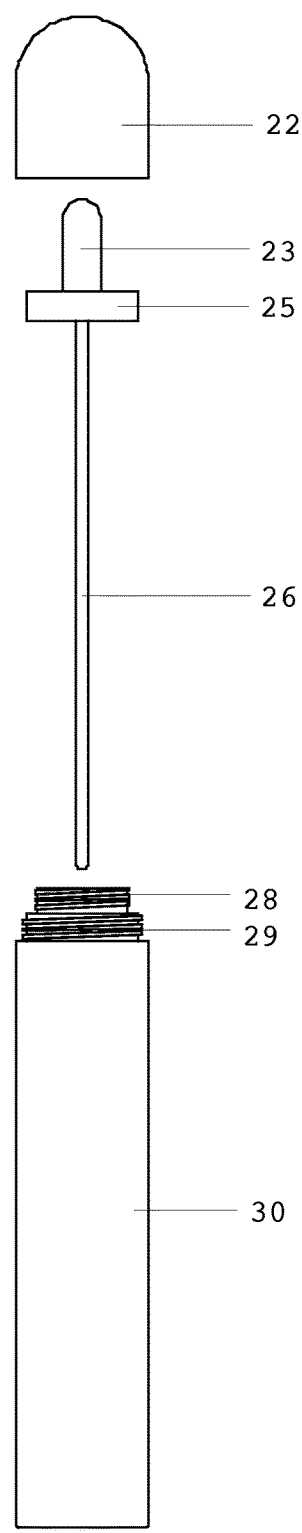
FIG. 8A is a exploded view of a basic exemplary embodiment of lubrication bottle embed with a transfer pipette.
Figure 8B:
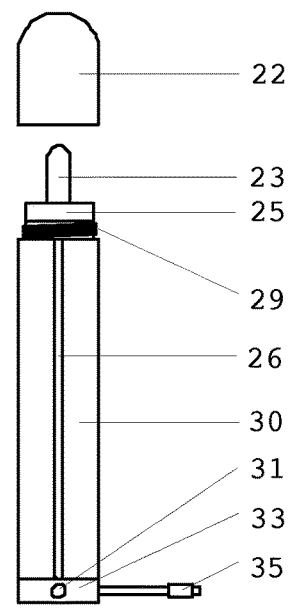
FIG. 8B is a exploded view of one exemplary embodiment of lubrication bottle embed with a transfer pipette and heating function, which is provided by USB power.
Figure 8C:
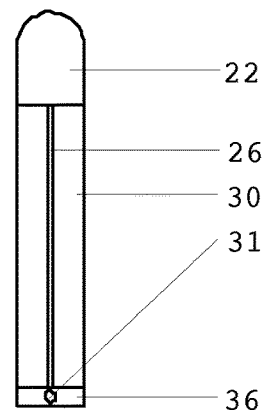
FIG. 8C is a front view of another exemplary embodiment of lubrication bottle embed with a transfer pipette and heating function, which is provided by wireless electrical power.

The kettle could have a top lid 1 to preserve heat or/and make it discreet (FIG. 1). Then there's a button 2 on the handle 3 to pop up the lid. The kettle could also just be simple without top lid (FIG. 2).

The kettle has a power switch 5 and a temperature controlling knob 6. The kettle also has a temperature controlling circuit and thermo sensors to toggle off the power switch after the water in chambers is ready to heat the masturbators, and to start heating when the water temperature is below user's setup.

The kettle has a marked scale (not shown) on the part 11 of the handle 3, for users to control the thermal capacity of water for heating in practical using.

The coaster has a wire and a plug 18 which could be hidden by rolled up under the coaster. 15, 19 are contacts between the electric heating base 8 and the coaster 16. The kettle is electric heated from house current from the power cord 18.

The transfer pipette has a long, thin tube 26 to release the lubrication at the bottom of the inner passage, and keep the passage tight as long as possible.

The transfer pipette could also be embed with lubrication bottle, which has a removable lid 22 to protect the bulb 23 of the transfer pipette from being impacted unexpectedly. The transfer pipette has a holder 25 which could be engaged with top end 28 of the lubrication bottle body 30 by screw connection. The removable lid 22 could also be engaged with top end 29 of the lubrication bottle body 30 by screw connection.

The lubrication bottle could also be embed with a wire electric heating base 33 or a wireless electric heating base 36. The electric heating base 33 or 36 has a temperature controlling knob 31 to turn on/off electric power and customize the final constant temperature. The wire electric heating embodiment has a USB plug 35 to provide electric power.

The electrical thermometer (FIG. 6) has a long, thin probe to reach the bottom of inner passage of masturbator, and keep the passage tight as long as possible.

The chambers 9, 21 and the nozzle 10 could be made of metal or plastic. The lid 1 and button 2 (if exists), the handle 3, the power switch 5 and the temperature controlling knob 6, the electric heating base 8 and coaster 16 should be made of, or covered with insulating material so as to protect the users from getting burned. The lubrication bottle 30 is made of transparent material.

For masturbator with only one sigle orifice, it's simple to use the device:

1. Fill the chambers 9 with some water. Use the aforementioned marked scale to control thermal capacity, and accommodate different sizes of masturbators*;

*For big masturbator like Fleshlight™ sleeve, it needs more thermal capacity of the heating water in masturbator chambers to make masturbator hot enough, but it only needs less thermal capacity of the water in masturbator chambers to make masturbator hot enough.

2. Put the kettle on the coaster 16 and connect the power cord 18 to house current.
3. Toggle on the power switch 5 to heat the water in chambers.
4. Use the temperature controlling knob 6 to customize the final constant temperature of the water in chambers.

5. The embodiment with a lid (FIG. 1) could boil the water. Another embodiment without lid (FIG. 2) would heat the water to nearby boiling point. Temperature controlling circuit will toggle off the power switch 5 after it's ready to heat the masturbators.
6. Fill lubrication into the passages of masturbators with the transfer pipette.
7. Open the lid 1 with the button 2 (if exists). Put each masturbator in different chamber 9. Close the lid 1 (if exists).
8. Wait. Use the electrical thermometer (FIG. 6) to customize the temperature inside the passage of masturbators. Use the timer 20 to make semi-automatical prompt when the masturbators are ready for use**.

**In view of different sizes, weights, thermal capacities of different masturbators and the users' diversities on definitions of hot, there is no easy way to provide consistent inner temperature automatically.

9. Have fun with the first masturbator. If the first one is getting cold, switch to the second one, and so on.

For masturbator with two orifices on both ends of the insertion passage, use the device this way:
1. Fill the chambers 9 with some water. Use the aforementioned marked scale to control thermal capacity, and accommodate different sizes of masturbators;
2. Put the kettle on the coaster 16 and connect the power cord 18 to house current.
3. Toggle on the power switch 5 to heat the water in chambers.
4. Use the temperature controlling knob 6 to customize the final constant temperature of the water in chambers.
5. The embodiment with a lid (FIG. 1) could boil the water. Another embodiment without lid (FIG. 2) would heat the water to nearby boiling point. Temperature controlling circuit will toggle off the power switch 5 after it's ready to heat the masturbators.
6. Open the lid 1 with the button 2 (if exists). Put each masturbator in different chamber 9. Close the lid 1 (if exists).
7. Wait. Use the electrical thermometer (FIG. 6) to customize the temperature inside the passage of masturbators. Use the timer 20 to make semi-automatical prompt when the masturbators are ready for use.
8. Fill hot lubrication which is prepared in lubrication chamber 21, or prepared by lubrication bottle which is embed with heating function (FIG. 8B or FIG. 8C), into the passages of masturbators with the transfer pipette.
9. Have fun with the first masturbator. If the first one is getting cold, switch to the second one, and so on.

Previous descriptions are only embodiments of the present invention and are not intended to limit the scope of the present invention. Many variations and modifications according to the claims and specification of the disclosure are still within the scope of the claimed invention. In addition, each of the embodiments and claims does not have to achieve all the advantages or characteristics disclosed. Moreover, the abstract and the title only serve to facilitate searching patent documents and are not intended in any way to limit the scope of the claimed invention.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

I claim:
1. A device for providing persistent hot tactile experience in male masturbation, comprising:
   an electric heating kettle having at least two masturbator chambers to contain and water-bath heat masturbators, a lubricant chamber to contain and heat lubricant, said lubricant chamber is separated from said masturbator chambers and a nozzle;
   a coaster having a wire and a plug to connect to house current;
   an electrical thermometer to measure temperatures of said masturbators.
2. The device according to claim 1, wherein the kettle has a marked scale for users to control water capacity and thermal capacity thereof, and accommodate different sizes of masturbators, by applying more water to heat bigger masturbators with consistent speed.
3. The device according to claim 1, wherein the kettle has a power switch, and a temperature controlling knob to customize a final constant temperature of the water-bath therein.
4. The device according to claim 1, wherein the kettle has a timer to prompt the user when masturbators are ready for use.
5. The device according to claim 1, wherein the kettle has a top lid and a button to pop up the lid.
6. The device according to claim 1, wherein the kettle has a temperature controlling circuit and thermo sensors to toggle off the power switch after the water in chambers is ready to heat the masturbators, and to restart heating when the water temperature is below user's setup.
7. A method for providing persistent hot tactile experience in male masturbation, comprising:
   c. setup a target temperature and start to heat water in masturbator chambers, and lubricant in lubricant chamber, said lubricant chamber is separated from said masturbator chambers;
   d. put masturbators in said masturbator chambers and start to water-bath heat said masturbators;
   e. utilize a temperature controlling circuit and thermo sensors to restart heating when the water temperature is below the user's setup;
   f. prompt user by a timer that all the masturbators reached a temperature which the user prefer;
   g. use one of the masturbators which is hot now, switch to the next hot masturbators when the current cools off;
   h. repeat step g, until the user finishes masturbating;
   i. customizing water capacity and thermal capacity thereof, and accommodate different sizes of masturbators, by applying more water to heat bigger masturbators with consistent speed.

* * * * *